(12) United States Patent
Looijen

(10) Patent No.: US 10,527,532 B2
(45) Date of Patent: Jan. 7, 2020

(54) GEOTECHNICAL APPARATUS HAVING BENDINGS/STRAIGHTENING DEVICE EQUIPPED WITH SETS OF ROLLERS

(71) Applicant: Fugro Engineers B.V., Nootdorp (NL)

(72) Inventor: Peter Nicolaas Looijen, Nootdorp (NL)

(73) Assignee: FUGRO ENGINEERS B.V., Nootdorp (NL)

( * ) Notice: Subject to any disclaimer, the term of this patent is extended or adjusted under 35 U.S.C. 154(b) by 60 days.

(21) Appl. No.: 15/724,524

(22) Filed: Oct. 4, 2017

(65) Prior Publication Data

US 2018/0156704 A1 Jun. 7, 2018

(30) Foreign Application Priority Data

Oct. 6, 2016 (NL) ..................................... 2017585

(51) Int. Cl.
| | | |
|---|---|---|
| *G01N 3/48* | (2006.01) | |
| *E21B 19/22* | (2006.01) | |
| *E21B 19/086* | (2006.01) | |
| *E21B 17/20* | (2006.01) | |

(52) U.S. Cl.
CPC ..................................... *G01N 3/48* (2013.01)

(58) Field of Classification Search
CPC ........ B21F 1/02; E21B 17/1035; E21B 19/00; E21B 41/00; E21B 17/003; E21B 17/206; E21B 19/22; E02D 1/022; E02D 1/02
See application file for complete search history.

(56) References Cited

U.S. PATENT DOCUMENTS

| | | |
|---|---|---|
| 3,379,052 A | 4/1968 | Howard et al. |
| 4,499,954 A | 2/1985 | Diggle |
| 6,412,560 B1 | 7/2002 | Bernat |
| 6,527,055 B1 | 3/2003 | Gipson |
| 2003/0010505 A1* | 1/2003 | Gipson ................... E21B 19/22 166/384 |
| 2003/0075361 A1* | 4/2003 | Terry ....................... G01V 3/30 175/61 |

(Continued)

FOREIGN PATENT DOCUMENTS

| | | |
|---|---|---|
| CA | 890288 | 1/1972 |
| EP | 0803638 | 10/1997 |

(Continued)

*Primary Examiner* — Brandi N Hopkins
(74) *Attorney, Agent, or Firm* — Peacock Law P.C.; Janeen Vilven

(57) ABSTRACT

A geotechnical apparatus comprising a holder with a coiled rod with a probe, such as a penetrometer, a rod bending/straightening device and a drive unit for both uncoiling the coiled continuous rod and pushing the uncoiled rod with the probe into the ground and for pulling such a rod with the probe out of the ground and recoiling the continuous rod, wherein the drive unit comprises two grippers to alternatingly grip the rod and move it along its longitudinal axis over a predefined length, the bending/straightening device has a first set of rollers, at least two of which are at one side of the rod and the remaining rollers are at an opposing side of the rod, such that the rollers convert the coiled rod to an essentially straight rod when uncoiling and convert the straight rod to a coiled rod of essentially constant coil diameter when coiling.

7 Claims, 3 Drawing Sheets

(56) References Cited

U.S. PATENT DOCUMENTS

| | | | |
|---|---|---|---|
| 2005/0133228 A1* | 6/2005 | Shampine | E21B 19/22 166/382 |
| 2011/0154908 A1 | 6/2011 | Mckee et al. | |
| 2011/0289994 A1 | 12/2011 | Smith et al. | |

FOREIGN PATENT DOCUMENTS

| | | |
|---|---|---|
| EP | 3173531 | 5/2017 |
| WO | 2005061842 | 7/2005 |

* cited by examiner

GEOTECHNICAL APPARATUS HAVING BENDINGS/STRAIGHTENING DEVICE EQUIPPED WITH SETS OF ROLLERS

CROSS-REFERENCE TO RELATED APPLICATIONS

This application claims priority to Netherlands Patent Application No. 2017585, filed on Oct. 6, 2016, and the specification and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The present invention relates to a geotechnical apparatus equipped for geotechnical investigation comprising a holder with a coiled rod wherein the rod is provided with a probe, such as a penetrometer, and the apparatus comprises a rod bending/straightening device and a drive unit for both uncoiling a the coiled continuous rod and pushing the uncoiled rod with the probe into the ground and for pulling such a rod with the probe out of the ground and recoiling the continuous rod, the apparatus being arranged for operation on land as well as on a sea floor, wherein the drive unit comprises two grippers arranged to alternatingly grip the rod and move it along its longitudinal axis over a predefined length.

Description of Related Art Including Information Disclosed Under 37 C.F.R. §§ 1.97 and 1.98:

U.S. Pat. No. 6,527,055 discloses a coiled tubing injection system for moving coiled tubing into or out of the well bore comprising: a coiled tubing injector; a static tubing gripper having a closed and an open position; and a movable tubing gripper having a closed and an open position, said movable tubing gripper being coaxially reciprocal between a first and a second position; wherein the coiled tubing injector, the static tubing gripper and the movable tubing gripper are positioned coaxially along the length of coiled tubing and are independently selectively operable. This known device is neither intended nor suited for geotechnical investigation, wherein the tubing would be provided with a probe such as a penetrometer.

The known system exhibits a number of disadvantages. The drive system is complex with a large number of moving parts, typically requiring proper sealing against ingress of sea water or debris. Further the uncoiling/coiling operation is rather crude. The uncoiling is accomplished by pulling the rod along a goose neck through a pulling force of the injector heads and supported by a back tension from the reel, while during coiling these roles are reversed. The reel is pulling and the injector heads are providing back tension. This results in most cases that the uncoiled rod will not be quite straight, which need not be a problem in existing wells, because inside the well, the rod is being guided by the wall of the well. The straightness of the rod obtained by the existing process is however clearly insufficient in geotechnical investigations wherein the rod is pushed into the ground without additional support and guiding. Also when recoiling wherein the pulling force is exerted by the reel, this results in a coil that requires additional holding elements added to the reel to maintain the coil diameter as soon as the back pulling disappears. These additional holding elements add to the complexity of the reel.

In addition, because the straightening as well as the coiling is accomplished by pulling the coil along the goose neck, this pulling force is relatively large and may lead to diameter changes of the rod. Also, the point contact of the drive unit with the rod during pushing and pulling requires a rather high maximum contact force applied at the rod to obtain sufficient friction to drive the rod. The probability of cold deformation of the rod to a smaller diameter is rather high, due to this high point contact force. This may be acceptable for applications where the rod is being coiled only very few times and where the recoiled rod is kept on the reel by additional holders, but is not acceptable in applications where frequent coiling/uncoiling has to take place, which is the case in the technical investigations. An example of such applications is typically found in sounding apparatuses for determining the penetration resistance of the ground as a function of depth, both on land as below a sea floor.

BRIEF SUMMARY OF THE INVENTION

It is an object of the present invention to provide for a geotechnical apparatus as mentioned in the first paragraph that does not or to a much lesser extent exhibit the disadvantages mentioned above.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
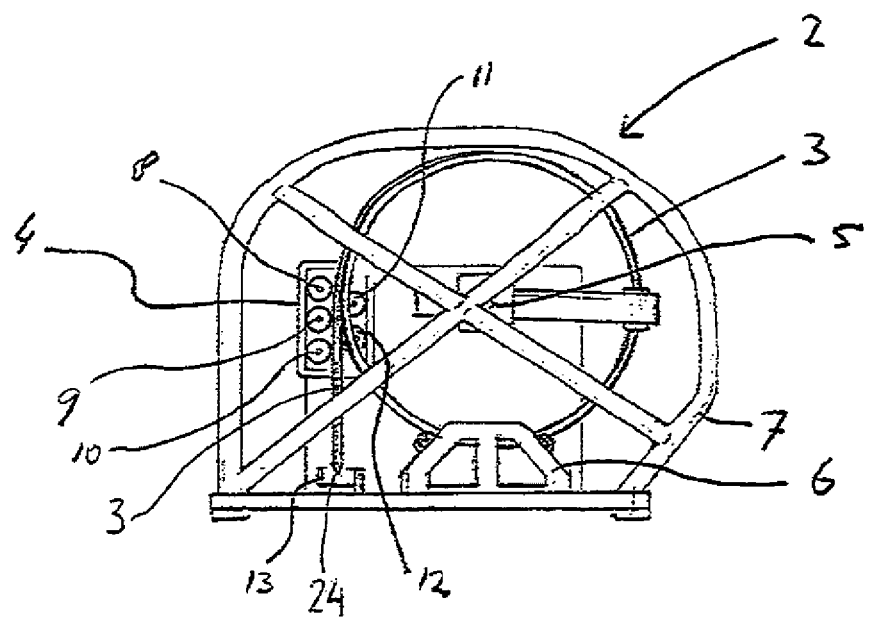
FIG. 1 shows a schematic view of a coiled tube on a coil holder and a bending/straightening device.

The above objects are met by an apparatus according to the preamble of claim 1, wherein the bending/straightening device is equipped with a first set of rollers of which at least two are positioned at one side of the rod and the remaining rollers form a second set of rollers positioned at an opposing side of the rod, so as to arrange that the rollers are arranged to convert the coiled rod to an essentially straight rod when uncoiling and are arranged to convert the straight rod to a coiled rod of essentially constant coil diameter when coiling.

Preferably at least one roll of the second set of rollers is in a different lateral position compared to the position of the first set of rollers, which promotes that a coil of essentially constant diameter at coiling is provided. The two grippers arranged to alternatingly grip the rod and move it along its longitudinal axis over a predefined length, provide sufficient pulling and pushing force using a driver with relatively few moving parts and of a simplified construction in comparison to the known injector heads.

The coiler/straightener with opposite rollers puts less requirements on the tensile force to be exerted by the drive unit, thus avoiding reduction of the rod diameter. In addition, the grippers of the driving unit according to the invention are in line contact with the rod when gripping. Thus, a much smaller contact force suffices to obtain sufficient friction as driving force. Hence the probability of plastic deformation and thus reduction of the rod diameter is much smaller.

In a preferred embodiment of the geotechnical apparatus according to the invention, the drive unit is arranged to move the rod with a constant movement. This means that stick/slip between the rod and the ground can be avoided and thus the friction is reduced.

By providing the gripping surfaces of each of the grippers to be in conformity to the surface of the rod, the ratio friction force/rod stress can be optimized, thus further reducing the possibility of reduction of rod diameter.

A relatively simple construction with few moving elements is obtained with a drive unit where the grippers each comprise two gripping elements that are movable between a rod gripping position and a rod releasing position. The low number of moving elements is advantageous if the unit is used on a sea floor, however the advantage remains although with less importance, if the unit is used on land.

Preferably the movements of the drive unit are driven by hydraulic means. This means the movements of the gripping elements as well as the movements of the grippers along the longitudinal axis of the rod.

In a preferred embodiment of the invention, the position of at least one of the rollers of the bending/straightening device is adjustable. This e.g. allows for adjusting the device to coils of different diameters, rods of different diameters or materials.

Test results have shown that for rods that are often used in geotechnical sounding of penetration resistance, with a bending/straightening device comprising multiple rollers as defined according to the invention good results concerning both straightness as well as consistency of coil diameter may be obtained.

The invention will now be further elucidated by the description of a not limiting example of an embodiment of the invention, referring to the drawings.

FIG. 1 shows a schematic view of unit 2 comprising a coiled rod 3 on a coil holder 6 and a bending/straightening device 4. The unit 2 comprises a protection frame 7 to protect the more sensitive elements of unit 2 e.g. during transport. Spindle 5 serves to guide the coiled rod 3 when coiling/uncoiling to the bending/straightening device 4. At its free end, the rod 3 supports a probe 24, which is essential for a geotechnical investigation unit 2 according to the invention.

Bending/straightening device 4 comprises in this exemplary embodiment five rollers 8-12, of which rollers 8, 9 and 10 form a first set of rollers situated on one side of the rod 3 and rollers 11 and 12 form a second set of rollers situated on the opposite side of the rod 3. It is to be noted that this exemplary embodiment satisfies the requirement according to the invention that at least two rollers are positioned at one side of the rod 3 and the remaining rollers are positioned at an opposing side of the rod 3. Accordingly, the rollers are arranged to convert the coiled rod 3 to an essentially straight rod when uncoiling, and are arranged to convert the straight rod to a coiled rod 3 of essentially constant coil diameter when coiling. The rollers 8-12 are positioned such that straightening will take place with the required accuracy of straightness when the rod is being pulled down (uncoiled) and when the rod is pushed up (as described with reference to the drive unit below), coiling of the rod will take place to the coil diameter required. For that purpose, at least one roll 11, 12 of the second set of rollers is in a different lateral position compared to the position of the first set 8, 9, 10 of rollers. Not all five rollers are equally loaded and the distribution of load will be different during coiling from the load distribution during straightening, as will be clear to the person skilled in the art. Unit 2 also includes a depth encoder 13 to register the extent to which the rod 3 has been pushed into the ground.

Figure 2:
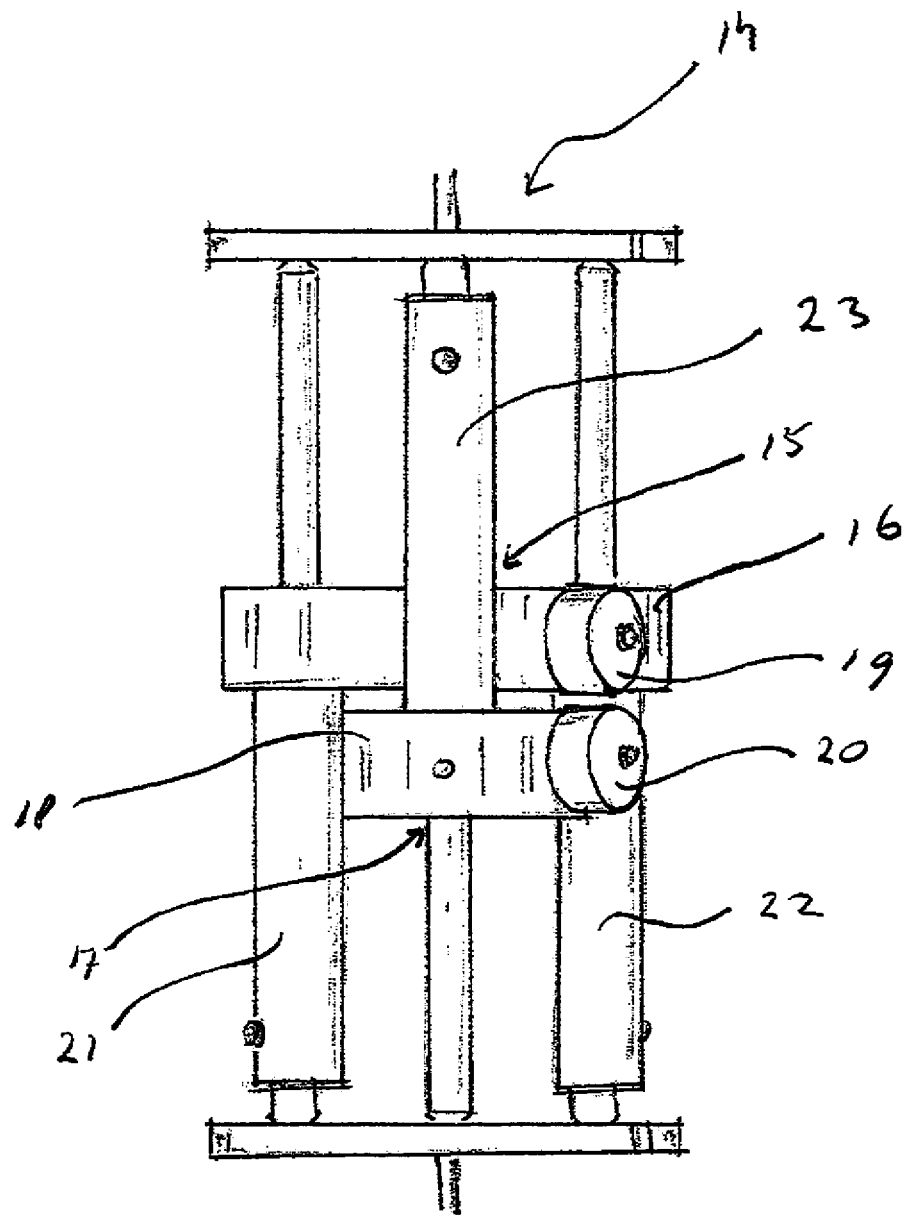
FIG. 2 shows a schematic view of a drive system, however without the rod to be driven.

FIG. 2 shows the drive unit, indicated in general with 14. For purposes of clarity, the rod to be driven by drive unit 14 has been omitted from FIG. 2. Drive unit 14 comprises two gripping/moving systems that are arranged to alternatingly grip the rod and move it along its longitudinal axis over a predefined length and thus essentially are moving in opposite directions. The gripping/moving systems each comprise a gripper, which are not visible in FIG. 2 but their respective positions are indicated by reference numerals 15 and 17. The first gripper 15 and second gripper 17 are each embedded in a gripper travel, respectively 16 and 18. Opening and closing of each gripper is driven by a clamp cylinder, first gripper 15 is opened and closed by clamp cylinder 19 and the second gripper 17 is opened and closed by clamp cylinder 20. The two assemblies, each formed by a gripper 15, 17, a gripper travel 16, 18 and a clamp cylinder 19, 20 are each being moved up and down by two feed cylinders. The assembly comprising the first gripper 15 is moved by feed cylinders 21 and 22, whereas from the assembly comprising the second gripper 17, only one feed cylinder 23 is visible in FIG. 2. The two grippers 15, 17 alternatingly are making a 'work stroke' in the desired direction of movement of the rod and a 'return stroke'. By controlling the speeds of movement during the 'work stroke' and the 'return stroke' as well as controlling the times of opening and closing the grippers, it is possible to ensure continuous movement of the rod, even at constant speed.

Figure 3:
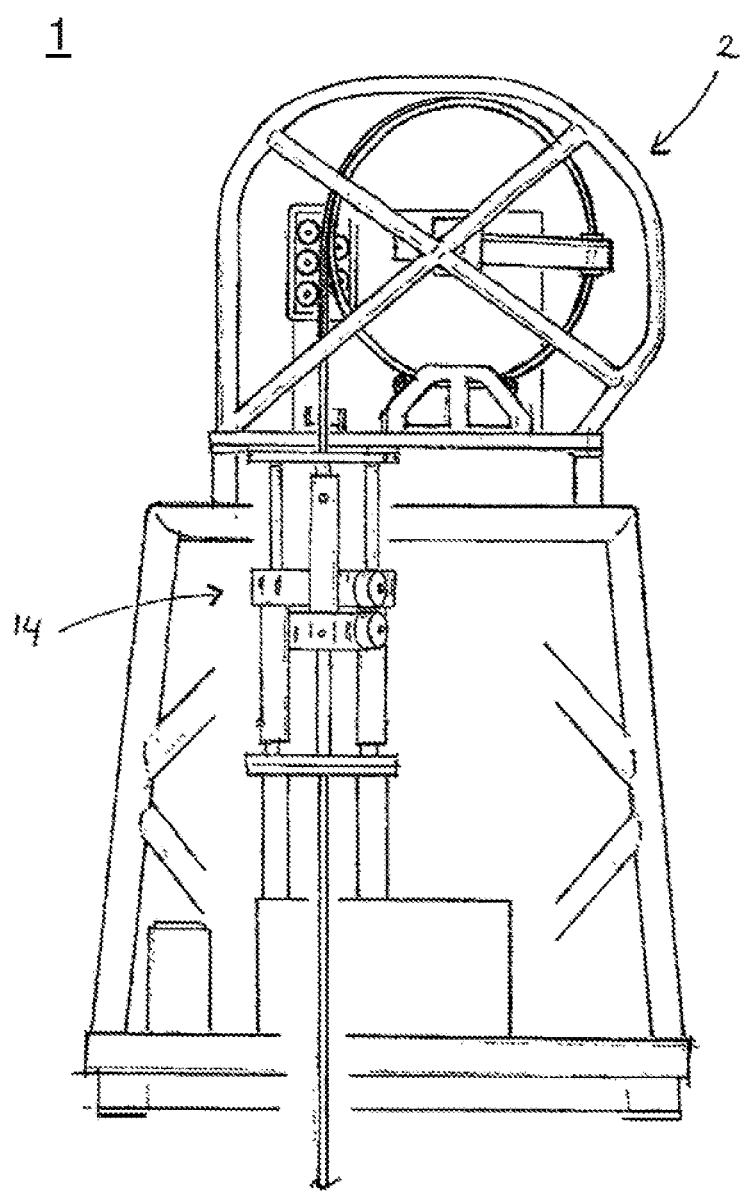
FIG. 3 show a schematic view of the geotechnical apparatus with the parts shown in FIGS. 1 and 2 mounted together.

FIG. 3 shows a geotechnical apparatus 1 with the unit 2 unit with coil holder and bending/straightening device and drive unit 14, as described above, being combined in a frame 7.

Although the invention has been discussed in the foregoing with reference to an exemplary embodiment of the apparatus of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

LIST OF APPLIED REFERENCE NUMBERS

1 Geotechnical apparatus
2 Unit with coil holder and bending/straightening device
3 Coil
4 Bending/straightening device
5 Spindle
6 Bottom support coil
7 Protection frame
8 Roller
9 Roller
10 Roller
11 Roller
12 Roller
13 Depth encoder
14 Drive unit
15 First gripper
16 Gripper travel of first gripper 15
17 Second gripper
18 Gripper travel of second gripper 17
19 Clamp cylinder of first gripper 15
20 Clamp cylinder of second gripper 17
21 Feed cylinder of first gripper 15
22 Feed cylinder of first gripper 15
23 Feed cylinder of second gripper 17
24 Probe

What is claimed is:

1. Geotechnical apparatus equipped for pushing a rod with a probe into a ground without support and guidance from a well and for pulling the rod with the probe out of the ground for performing geotechnical investigation using a penetrometer, the apparatus comprising a holder with the rod wherein the rod is coiled on the holder, and the apparatus comprises a rod bending/straightening device and a drive unit for both uncoiling the coiled continuous rod during said pushing of the uncoiled rod into the ground and recoiling the uncoiled rod during said pulling of the rod out of the ground, the apparatus being arranged for operation on land as well as on a sea floor, wherein the drive unit comprises two grippers arranged to alternatingly grip the rod and move it along its longitudinal axis over a predefined length for performing the pushing and pulling,
    characterized in that the probe is the penetrometer, and in that the bending/straightening device is equipped with a first set of rollers of which at least two are positioned at one side of the rod and the remaining rollers form a second set of rollers positioned at an opposing side of the rod, so as to arrange that the rollers are arranged to convert the coiled rod to an essentially straight rod when uncoiling and are arranged to convert the straight rod to a coiled rod of essentially constant coil diameter when coiling.

2. The geotechnical apparatus according to claim 1, wherein at least one roll of the second set of rollers is in a different lateral position compared to the position of the first set of rollers.

3. The geotechnical apparatus according to claim 1, wherein the drive unit is arranged to move the rod with a continuous movement.

4. The geotechnical apparatus according to claim 1, wherein each of the grippers comprises gripping surfaces that are in conformity to the surface of the rod.

5. The geotechnical apparatus according to claim 1, wherein the grippers each comprise two gripping elements that are movable between a rod gripping position and a rod releasing position.

6. The geotechnical apparatus according to claim 1, wherein the movements of the drive unit are driven by hydraulic means.

7. The geotechnical apparatus according to claim 1, wherein the position of at least one of the rollers of the bending/straightening device is adjustable.

* * * * *